United States Patent [19]

Luo

[11] Patent Number: 4,479,900

[45] Date of Patent: Oct. 30, 1984

[54] 1-CARBALKOXYALKYL-3-ARYLOXY-4-(2'-CARBOXYPHENYL)-AZETIDIN-2-ONES

[75] Inventor: Tatao Luo, El Sobrante, Calif.

[73] Assignee: Chevron Research Company, San Francisco, Calif.

[21] Appl. No.: 490,065

[22] Filed: Apr. 29, 1983

[51] Int. Cl.³ .................. C07D 205/08; A01N 43/44; C07C 119/10; C07C 69/65
[52] U.S. Cl. .................. 260/239 A; 71/88; 560/51; 560/61; 560/62; 560/35; 562/471; 562/472; 260/544 D
[58] Field of Search .................. 260/239 A

[56] References Cited

U.S. PATENT DOCUMENTS 4,181,800  1/1980  Kamiya .................. 260/239 A

OTHER PUBLICATIONS

Sharma et al., Chem. Abs. 94, 102790r, (1980).

*Primary Examiner*—Mark L. Berch
*Attorney, Agent, or Firm*—S. R. LaPaglia; T. G. DeJonghe; S. L. Biggs

[57] ABSTRACT

Compounds of the formula:

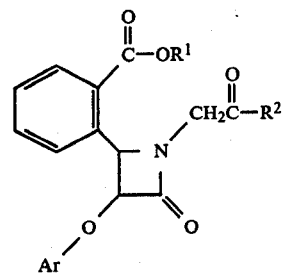

wherein $R^1$ is lower alkyl or benzyl. $R^2$ is lower alkoxy, benzyloxy, or the group

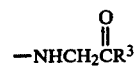

where $R^3$ is lower alkoxy; and Ar is phenyl optionally substituted with 1 to 3 substituents independently selected from halogen, trihalomethyl, nitro or lower alkyl, show plant growth regulating activity.

14 Claims, No Drawings

1-CARBALKOXYALKYL-3-ARYLOXY-4-(2'-CARBOXYPHENYL)-AZETIDIN-2-ONES

BACKGROUND OF THE INVENTION

The present invention relates to 1-carbalkoxyalkyl-3-aryloxy-4-(2'-carbalkoxyphenyl)-azetidin-2-ones activity as plant growth regulators and as herbicides.

The commonly assigned patent application Ser. No. 225,886 of Francis J. Freenor III discloses compounds of the formula:

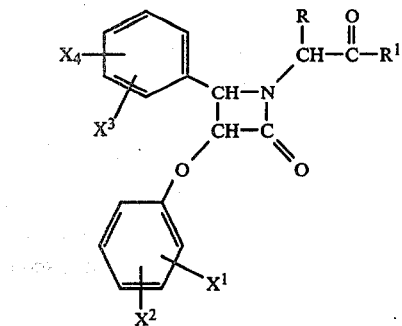

wherein R is hydrogen or alkyl of 1 to 3 carbon atoms; $R^1$ is hydrogen, alkyl of 1 to 6 carbon atoms, alkoxy of 1 to 6 carbon atoms, alkythio of 1 to 6 carbon atoms or $NR^1R^2$ wherein $R^1$ and $R^2$ are independently hydrogen or alkyl of 1 to 12 carbon atoms; and $X^1$, $X^2$, $X^3$ and $X^4$ are independently hydrogen, chloro, bromo, fluoro, iodo, alkyl of 1 to 4 carbon atoms or alkoxy of 1 to 4 carbon atoms, which are active as plant growth regulators.

The commonly assigned patent application Ser. No. 391,798 of Tatao Luo, Louis Russo and Francis J. Freenor III now U.S. Pat. No. 4,443,372 discloses 1-lower alkyl derivatives of 3-aryloxy-4-(2-carbalkoxy)-phenyl-azet-2-one compounds of the formula:

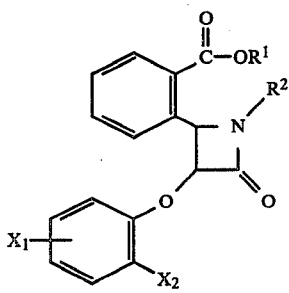

wherein $R_1$ is methyl or ethyl; $R_2$ is lower alkyl; and $X_1$ and $X_2$ are independently hydrogen or halogen which are active as plant growth regulators.

U.S. Pat. No. 4,181,800 discloses a large group of anti-microbial 2-azetidinone compounds of the general formula:

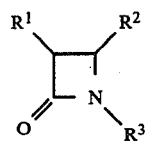

wherein $R^1$ is amino, substituted amino, substituted hydroxy, azido or halogen; $R^2$ is hydrogen, hydroxymethyl, aralkoxyaminomethyl, aryl, aralkenyl, formyl, carboxy, or a residue of a nucleophile; and $R^3$ is a group of the formula:

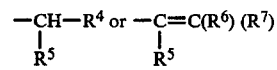

wherein $R^4$ is aryl, aralkyl, arylthioalkyl or a heterocyclic group; $R^5$ is carboxy or its derivative; $R^6$ is alkyl, haloalkyl, arylthio or heterocyclic-thioalkyl; and $R^7$ is hydrogen, haloalkyl or heterocyclic-thioalkyl; (subject to various provisos). The compounds are disclosed as useful antibiotics for treating microbial infections in mammals.

U.S. Pat. No. 4,207,234 discloses a large class of antimicrobial 4-unsubstituted azetidinone compounds which have the general formula:

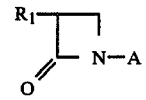

wherein $R_1$ is amino or acylamino; and A is hydrogen or the group:

wherein $R^x$ is hydrogen; $R^y$ is, in pertinent part, hydrogen or alkyl of up to 6 carbon atoms; and $R^2$ is, in pertinent part, carboxy, hydroxy, amino, cyano, or alkyl of up to 6 carbon atoms substituted by carboxy or a salt thereof. These compounds are disclosed as useful as antibiotics to treat microbial infections in mammals.

SUMMARY OF THE INVENTION

The compounds of my invention are represented by the formula:

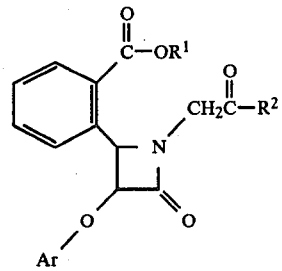

wherein $R^1$ is lower alkyl or benzyl; $R^2$ is lower alkoxy, benzyloxy or the group

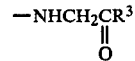

where $R^3$ is lower alkoxy and Ar is phenyl optionally substituted with 1 to 3 substituents independently selected from halogen, trihalomethyl, nitro, and lower alkyl.

Among other factors, the present invention is based on my finding that these compounds show surprising activity as plant growth regulators. In particular, these compounds exhibit a significantly higher level of activity than other structurally related compounds. In particular treatmtent of plants with the compounds of my invention may result in a saving of labor in the case of the plants, such as by decreasing the need for mowing turf or for physical pruning of fruit trees and ornamentals due to the compounds' herbistatic and chemical pruning activities. These compounds may also increase the yield in plants such as cucumbers by increasing both flowering and the proportion of female flowers. The plant growth regulating (PGR) activities of these compounds appear to be very susceptible to structural change, such that while the compounds of this invention having a carbalkoxy group in the ortho position on the 4-phenyl group show unexpectedly good PGR activity, corresponding compounds having the carbalkoxy groups in the meta or para position show significantly less PGR activity. It is believed that the trans isomer of these compounds, that is, where the 3-phenoxy and the 4-phenyl groups are in the trans position, has greater PGR activity than the corresponding cis isomer.

As is apparent, the compounds have asymmetric carbon atoms and thus can exist as optical and geometric isomers. Accordingly, the respective optical isomers and geometric isomers, as well as mixtures thereof, are encompassed within the invention.

Preferred $R^1$ groups include methyl and ethyl.

Preferred $R^2$ groups include methoxy, ethoxy and the group

$$-NHCH_2CR^3$$

where $R^3$ is lower alkoxy.

Preferred Ar groups include phenyl groups optionally substituted with up to two halogen atoms. Especially preferred AR groups are phenyl groups having a halogen atom in the para position. Most especially preferred Ar groups are those where the halogen substituent is fluorine.

As used herein, the following terms have the following meanings, unless expressly stated to the contrary.

The term "alkyl" refers to both straight- and branched-chain alkyl groups. The term "lower alkyl" refers to both straight- and branched-chain groups having a total of from 1 to 3 carbon atoms and includes primary and secondary alkyl groups. Typical lower alkyls include, for example, methyl, ethyl, n-propyl, isopropyl, and the like.

The term "halo" or "halogen" refers to the groups fluoro, chloro, bromo, and iodo.

The term "lower alkoxy" refers to the group OR' where R' is lower alkyl. Typical lower alkoxy groups include methoxy, ethoxy and the like.

The term "carbalkoxy" refers to the group

where R' is an alkyl group. The term "lower carbalkoxy" refers to carbalkoxy groups where R' is a lower alkyl group. Typical carbalkoxy groups include carbomethoxy, carboethoxy, and the like.

The terms "plant growth regulator" and "plant growth regulating" refer to compounds and/or their activities which alter growth or development of a plant as by a direct or indirect effect on natural phytohormone systems which may result in a beneficial increase or decrease in growth rate of the entire plant or a specific plant organ, or by helping a plant to adjust to stress, as by increased tolerance to drought, salt or wind. These growth regulating effects include, but are not limited to, increased branching, bud break at nodes which do not normally produce branches, increased or decreased set of flowers, reduction of stem height, preventing or retarding the growth of lateral buds, and promotion of the thinning out of superfluous fruits in various fruit trees.

DETAILED DESCRIPTION OF THE INVENTION

The compounds of the present invention may be prepared according to the following reaction sequence:

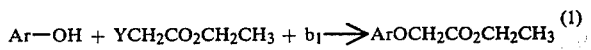
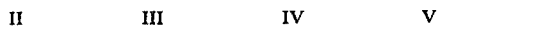
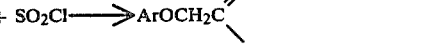
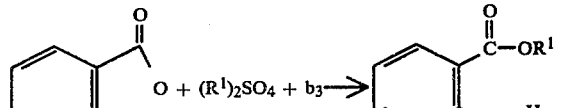

wherein $R^1$, $R^2$ and Ar are as previously defined in conjunction with formula I, Y is chlorine or bromine, and $b_1$, $b_2$ and $b_3$ are bases.

Reaction (1) is conducted by combining approximately equimolar amounts of II, III and IV in solvent. Suitable bases, $b_1$, include inorganic bases such as potassium carbonate, and the like. Suitable solvents include inert organic solvents such as methyl ethyl ketone, acetone, toluene, other hydrocarbon solvents, and the like. The reaction is conducted at a temperature of about 20° to about 110° C., preferably from about 40° to about 80° C. and is generally complete within about 2 to about 10 hours. For convenience, the reaction may be carried out at ambient pressure. The product, V is isolated by conventional precedures such as filtration, evaporation under vacuum, and the like or alternatively after being filtered and stripped is used in reaction (2) without further isolation.

Some compounds V are commercially available such as those where Ar is unsubstituted phenyl, parachlorophenyl 2,4-dichlorophenyl and 2,4,5-trichlorophenyl.

Reaction (2) is conducted by combining V and VI in solvent. It is preferred to use an excess of base, VI, preferably in the range of about 1½ to about 3 equivalents VI per equivalent V. Suitable bases, $b_2$, include strong inorganic bases such as potassium hydroxide, sodium hydroxide, and the like. Suitable solvents include lower alcohols such as ethanol, and the like. The reaction is conducted at a temperature of about 20° to about 120° C., preferably from about 60° to about 90° C., and is generally complete within 1 to about 4 hours. For convenience, the reaction may be carried out at ambient pressure. The product, VII, is isolated by conventional procedures such as stripping, extraction, and the like.

Reaction (3) is a conventional preparation of an acid chloride IX from the corresponding carboxylic acid, VII, using reagents well-known to those skilled in the art. For convenience, thionyl chloride, VIII, is used. Other suitable reagents include oxalyl chloride and the like. The reaction is conducted by combining approximately equimolar amounts of VII and VIII in solvent, although it is preferred to use a slight excess of VIII. The reaction is conducted at about 40° to about 150° C., preferably from about 80° to about 120° C., such as at reflux; and is generally complete within about ½ to about 3 hours. Suitable solvents include inert organic solvents such as toluene, benzene and the like. The product, IX, is isolated by conventional procedures such as stripping and the like, or alternatively, after removal of excess thionyl chloride, used in Reaction (6) without further isolation.

Reaction (4) is conducted by combining X, XI and XII in solvent. It is preferred to slowly add XII to a stirred mixture of X and XI in solvent. It is preferred to use an excess of XI and XII in relation to X, on the order of about 1 to about 3 moles of XI per mole X and about 1 to about 3 moles of XII per mole X. Suitable bases, $b_3$, include organic bases such as triethylamine, pyridine, and the like. The reaction is conducted at a temperature of about 30° to about 80° C., preferably about 40° to about 60° C. or at reflux, and is generally complete within about 1 to about 3 hours. Suitable solvents include inert organic solvents such as methylene chloride, benzene, and the like. The product, XIII, is isolated by conventional procedures such as extraction, washing, drying, stripping, and the like.

Reaction (5) is conducted by adding XIII to XIV and XV in solvent. Although approximately equimolar amounts of XIII and XIV may be used, it is preferred to use a very slight excess of XIII. It is also preferred to add an approximately equimolar amount of anhydrous magnesium sulfate XV to the XIV-solvent mixture to remove water formed during the reaction. Alternatively, rather than using magnesium sulfate, the water formed during the reaction may be removed using other reagents or physical means well-known to those skilled in the art. The amino acid XIV is normally used as a salt, such as a hydrochloride or tosylate, rather than as the free acid. The free acid is generated in situ by treatment with a base XII such as triethylamine. It is preferred that an excess of XII be used, about 1 to about 3 equivalents XII per equivalent XIV, preferably on the order of about 2 equivalents XII per equivalent XIV. The reaction is conducted at a temperature of about 0° to about 100° C., preferably from about 30° to about 50° C. or at reflux, and is generally complete within about 1 to about 3 hours. Suitable solvents include inert organic solvents such as methylene chloride, benzene, and the like. The product, XV, is isolated by conventional procedures such as filtration, concentration, and the like. It is preferred to use XVI right away in Reaction (6).

Reaction (6) is conducted by combining IX, XVI and XII in solvent. Although approximately equimolar amounts of IX, XVI and XII may be used, it is preferred to use a slight excess of IX and XII in relation to XVI. The reaction is conducted at a temperature of about 0° to about 100° C., preferably from about 40° to about 80° C., and is generally complete within about 1 to about 3 hours. The product, I, is isolated by conventional procedures such as extraction, washing, concentration, trituration, and the like. Reaction (6) may produce a mixture of cis and trans isomers. The geometric isomers may be separated by conventional separation processes such as chromatography.

Reaction (6) may produce a mixture of geometric isomers. The conditions under which the reaction is conducted may influence which geometric isomer(s) is produced, and if a mixture is produced the relative ratio of trans:cis. It is believed that factors such as the solvent used, the temperatures at which the addition of the reactants and the reaction itself are conducted and the order in which the reactants are combined may effect which isomer or isomers are formed. Thus, where n-hexane is the solvent used, a cis:trans isomer mixture is generally produced, whereas when the solvent is methylene chloride, benzene or toluene, formation of the trans isomer is favored. Conducting the reaction at a high temperature (e.g. reflux) especially at about 80° C., after the reactants have been combined generally favors formation of the trans isomer. Adding XVI to IX in solvent followed by addition of XII favors formation of the trans isomer. Thus, if XVI is added to IX in solvent at 0° C., followed by addition of XII and then heating the reaction mixture to reflux, predominately trans isomer is produced.

UTILITY

The compounds of the present invention are surprisingly active as plant growth regulators, and may effect plant growth in a variety of ways.

The plant growth regulating effects (PGR) of the present invention include herbistatic activity and thus, they may retard growth in plants such as grasses (requiring less frequent mowing) bedding plants and trees. The compounds may also be used as chemical pruning agents for plants such as fruit trees and bushy ornamentals. The compounds may be used as preconditioning agents for defoliation by promoting abscission and as agents for preventing late growth in crops such as cotton. Other PGR effects include increasing flowering and also effecting sex expression in flowering, for example increasing the number of female flowers and thus the number of fruits produced in plants such as cucumbers. Other PGR effects are evidenced in the biological testing data in Table II.

Some of the compounds of this invention also show herbicidal activity.

A further understanding of my invention may be found in the following non-limiting examples.

EXAMPLE 1: Preparation of

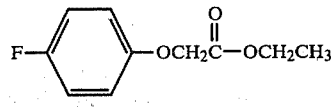

Ethyl para-fluorophenoxyacetate

A mixture of 13.8 g (0.1 mole) potassium carbonate, 11.3 g (0.01 mole) 4-fluorophenol and 13.0 ml (19.6 g [0.22 mole]) ethyl bromoacetate in 100 ml methyl ethyl ketone were stirred overnight at room temperature and then heated at reflux for 5 hours. After the reaction mixture cooled to room temperature, it was filtered. The filtrate was concentrated to remove solvent. The concnetrate was used as a whole without further isolation in Example 2.

EXAMPLE b 2: Preparation of

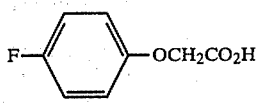

Para-fluorophenyoxyacetic acid

A mixture of ethyl para-fluorophenoxyacetate, the product of Example 1, (approximately 22.0 g (0.1 mole)) and 20.0 g (0.3 mole) potassium hydroxide in 100 ml absolute ethanol was heated at reflux for three hours, cooled to room temperature and then stripped. The residue was taken up in 300 ml water. The aqueous solution was washed with 200 ml ether, acidified to give a pH of about 1 with concentrated hydrochloric acid and extracted a second time with ether. The second ethereal extract was washed with 200 ml water, dried with anhydrous magnesium sulfate and then concentrated to give 16.4 g of the product.

EXAMPLE 3: Preparation of

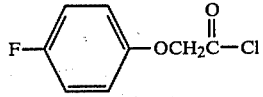

Para-fluorophenoxyacetyl chloride

Into a 100 ml round bottom flask equipped with a magnetic stirrer, reflux condenser equipped with a connector to a 50% sodium hydroxide trap, 6.81 g (0.040 mole) para-fluorophenoxyacetic acid (the product of Example 2), 2.96 ml (0.044 mole) thionyl chloride, and about 40 ml toluene. The reaction mixture was stirred at reflux for two hours, allowed to cool to room temperature, and then concentrated to give 7.2 g of the product, a brwon liquid.

EXAMPLE 4: Preparation of

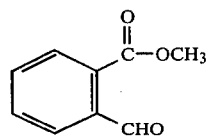

2-Carbomethoxybenzaldehyde

Into a 3-neck 1 liter round bottom flask equipped with a magnetic stirrer, reflux condenser fitted with a drying tube, addition funnel with a septum and a nitrogen inlet, 100 g (0.659 mole) 2-carboxybenzaldehyde, about 140 ml methylene chloride and 162.8 g [122.2 ml (1.291 moles)] dimethylsulfate were placed. The mixture was heated to reflux 135.89 g [187.2 ml (1.343 moles)] triethylamine was added dropwise, maintaining a brisk reflux. After the addition was complete, the resulting gold-colored solution was allowed to cool to room temperature, and then washed with 400 ml water. After the layers were separated, the aqueous phase was extracted with 400 ml methylene chloride. The organic layers were combined and washed with 500 ml of a saturated aqueous sodium bicarbonate solution and with 500 ml water. The organic phase was dried over magnesium sulfate and then concentrated to give 111.5 g of the product as a gold liquid.

EXAMPLE 5: Preparation of

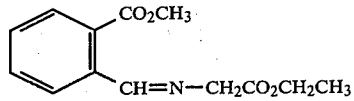

Ethyl [N-2-carbomethoxybenzylidenyl]glycine

Into a 3-neck 250 ml round bottom flask equipped with a magnetic stirrer, reflux condenser filled with a drying tube and an addition funnel fitted with a septum and a nitrogen inlet, were added in order 6.77 g (0.048 moles) glycine ethylester hydrochloride, about 6 g (>0.052 mole) anhydrous magnesium sulfate, and 75 ml methylene chloride. The mixture was cooled to 0° C. and 9.92 g (136.7 ml [0.098 mole]) triethylamine were added dropwise, followed by the dropwise addition of 8.56 1 g (0.052 mole) of 2-carbomethoxybenzaldehyde (the product of Example 4). The reaction mixture was then heated, stirred at reflux for two hours, and then allowed to cool to room temperature. The magnesium sulfate was removed by filtration using a Buchner funnel. The filtrate was concentrated and the resulting slurry taken up with about 50 ml benzene. The white solid was removed by filtration using a Buchner funnel. Concentration of the filtrate gave 10.6 g of product as a gold liquid.

EXAMPLE 6: Preparation of

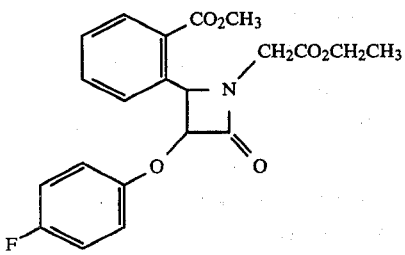

1-Carboethoxymethyl-3-para-fluorophenoxy-4-[2'-carbomethoxyphenyl]-azet-2-one (a) Into a 100 ml round bottom flask equipped with a magnetic stirrer, reflux condenser fitted with a drying tube, addition funnel with a nitrogen inlet and a thermometer were added about 10 ml benzene, and 4.41 g (0.023 moles) para-fluorophenoxyacetyl chloride (the product of Example 3); after cooling to 0° C., 5.3 g (0.021 mole) ethyl [N-2-carbomethoxybenzylidenyl]glycine (the product of Example 5) in about 2 ml benzene was added dropwise through the addition funnel. The resulting mixture was stirred at 0° C. for a half hour; then b 2.83 g (3.90 ml [0.028 mole]) triethylamine were added. The resulting mixture was stirred at reflux for one hour and then stirred overnight at room temperature. The reaction mixture was then taken up with 100 ml each of ether and water. The layers were separated and the ether layer washed with 100 ml each of a saturated aqueous sodium bicarbonate solution and water. Drying of the ether fraction with anhydrous magnesium sulfate followed by concentration gave 7.3 g of crude product as a brown gum.

(b) The crude product from step (a) was cleaned up (purified) by dry column chromatography by the following procedure:

In a vessel, 7.3 g of the product from step (a), 16 g silica gel and about 30 ml methylene chloride were placed and stirred. The resulting slurry was stripped to give a free-flowing solid.

The resulting solid was loaded on a 100 cm×5 cm column packed with silica gel (activity III). The material was eluted with about 1.2 liters methylene chloride-:ethyl acetate (about 19:1).

The shorter traveling band was isolated and eluted with about 200 ml to about 400 ml ethyl acetate. Stripping of the ethyl acetate gave 1.3 g of the product (trans isomer) as an amber gum.

Elemental analysis for $C_{21}H_{20}NO_6F$ showed: calculated %C 62.84, %H 5.02, and %N 3.49; found %C 60.09, %H 5.32, and %N 3.2.

EXAMPLE 7: Preparation of

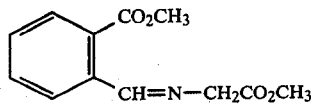

Methyl ]N-2-carbomethoxybenzylidenyl]glycine

Into a 250 ml round bottom flask equipped with a magnetic stirrer, reflux condenser fitter with a drying tube, and an addition funnel with a nitrogen inlet, were added 6.66 g (0.0525 mole) glycine methyl ester HCl, about 7 g (about 0.058 mole) anhydrous magnesium sulfate and about 75 ml methylene chloride. After the resulting mixture was cooled to 0° C., 10.75 g (14.8 ml [0.106 mole]) triethylamine was added dropwise, followed by the dropwise addition of 9.19 g (7.54 ml [0.056 mole]) 2-carbomethoxybenzaldehyde. The reaction mixture was heated and then stirred at reflux for 2 hours. The reaction mixture was allowed to cool to room temperature. The magnesium sulfate was filtered off with a Buchner funnel; the resulting slurry was taken up with 50 ml benzene. The triethylamine hydrochloride salt was removed by filtration with a Buchner funnel. The filtrate was concentrated to give 12.2 g of the product as a gold oil.

EXAMPLE 8: Preparation of

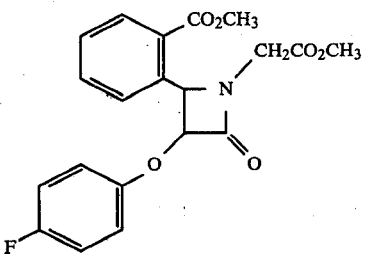

1-Carbomethoxymethyl-3-para-fluorophenoxy-4-[2'-carbomethoxyphenyl]-azet-2-one (a) Into a 100 ml round bottom flask, equipped with a magnetic stirrer, reflux condenser and an addition funnel with a nitrogen inlet, 21.6 g (0.114 mole) parafluorophenoxyacetyl chloride, and 50 ml methylene chloride were placed. After cooling to 0° C., 24.5 g (0.104 mole) methyl [N-2-carbomethoxybenzylidenyl]glycine was added. The resulting mixture was stirred at 0° C. for one half hour; then 10.52 g (14.5 ml [0.125 mole]) triethylamine were added. The reaction mixture was heated, stirred at reflux for two and one half hours, and then stirred overnight at room temperature. The mixture was taken up with 100 ml each of methylene chloride and water. The layers were separated, and the organic layer was washed with 100 ml each of a saturated aqueous sodium bicarbonate solution and water. The organic phase was dried over anhydrous magnesium sulfate and concentrated to give 40.6 g of crude product as a black gum.

(b) The crude product from step (a) was purified by dry column chromatography by the following procedure:

In a vessel, about 13 g of the product of step (a), 20 g silica gel and about 50 ml methylene chloride were placed and stirred. The resulting slurry was stripped to give a free-flowing solid.

The resulting solid was loaded on an 120 cm×5 cm column packed with silica gel (activity III). The material was eluted with about 1.5 liters of methylene chloride:ethyl acetate (15:1).

The band was with an Rf of about 0.5 was isolated and eluted with about 200 to about 500 ml ethyl acetate. The eluatate was stripped to give 6.6 g of an amber gum which solidified upon standing. The solid was triturated with ether:hexane 2:1; the resulting white solid was collected with a Buchner funnel, yielding 3.25 g of the product (trans isomer) as a white solid.

Elemental Analysis for $C_{20}H_{18}FNO_6$ showed: calculated %C 62.01, %H 4.68, and %N 3.62; found %C 62.82, %H 4.94, and %N 3.73.

Compounds which were made in accordance with Examples 1 to 8 using the appropriate starting materials are found in Table I.

EXAMPLE A

Axillary Bud Inhibition Foliar Spray

The compounds of this invention were tested to determine their effect on axillary bud growth of Pinto Beans.

Pinto Bean plants, one pot per test compound (one plant per pot) were sprayed with an acetone-water carrier solution which contained a small amount of nonionic emulsifier with a concentration of 200 ppm (or 625 ppm were noted) of test compound. A pot sprayed with the carrier solution without test compound was used as a check. One pot was sprayed with 100 ppm a-naphthyleneacetic acid as a standard. After spraying the solution was allowed to dry on the plant leaves; the plants were then transferred to a greenhouse maintained at 70°–80° F. and the plants were randomized.

The plants were read 12 days after treatment. Bud growth at the axil of the monofoliate leaf was read and expressed as % inhibition of axillary growth as compared to the untreated check topped above the monofoliate leaves. Results are given in Table II.

EXAMPLE B

Germination and Seedling Development Test

The compounds of this invention were tested to determine their effect on seed germination, seedling shoot and root development in two types of plant, mung beans and barnyard grass.

Seed pouches containing mung bean and barnyard grass seeds were treated with 15 ml of a solution containing 30 ppm (or 40 ppm where noted) of test compound in a water-acetone carrier formulation which contained a small amount of non-ionic emulsifier. A seed pouch treated with carrier formulation without test compound was used as a check. The seed pouches were then held under about 125–150 foot-candles of light for 24 hours per day for 7 days at room temperature.

Root length was measured for each species and expressed as % root inhibition as compared to the check. Results are given in Table II.

EXAMPLE C

Ethylene Evolution Test

The compounds of this invention were tested to determine their effect on ethylene evolution in plant tissue. Ethylene gas is a natural plant growth regulator which is produced by the plant when a change in growth or development occurs. Active levels of ehtylene production from the leaf disc explant system may indicate wounding or damage to the plant tissue, a change in the enzyme or hormonal balance within the leaf disc, the onset of senescence of the leaf, or an increase in the metabolic rate of the tissue.

Vials each with two leaf discs cut from the monofoliate leaf of the pinto bean were treated with one ml of a $10^{-5}$ b-benzylaminopurine solution (BAP) and one ml of a 80 ppm (or 100 ppm or 250 ppm where noted) acetone-water solution of test compound which contained a small amount of non-ionic emulsifier. After treatment, the vials were capped and the time of capping noted. The vials were then incubated for 18 hours at room temperature in diffuse light. Vials containing one ml of BAP and one ml of 2% aqueous acetone were used as checks.

After incubation, one ml of gas mixture is removed from the upper portion of the vial and tested with a gas chromatograph. The data is recorded as % of reference where reference is 5 ppm ethylene in nitrogen gas. Results are given in Table II.

EXAMPLE D

Cotton Defoliation, Desiccation and Regrowth Inhibition

The compounds of this invention were tested to determine their effect on defoliation, desiccation and regrowth of cotton.

Cotton plants 4 to 5 weeks old having 4 true leaves above the cotyledonary leaves from which growth beyond the second true leaf had been removed not longer than 24 hours before treatment were used as test plants. The plants are treated by spraying with a 2000 ppm solution of test compound in an acetone-water carrier formulation which contained a small amount of non-ionic emulsifier. A plant sprayed with carrier formulation without test compound was used as the untreated check. An hour after spraying, the plants were transferred to a greenhouse maintained at about 85° F. ($\pm 5°$ F.) where they were allowed to incubate for 13 to 18 days before evaluation.

Defoliation or desiccation of each of the four leaves on each plant was evaluated, each leaf being 25% of the total. The combined defoliation/desiccation percentages cannot exceed 100%, since a leaf which both abscises and desiccates is noted only as "Defoliation".

Regrowth was noted as % inhibition of axillary bud growth as compared to the untreated check.

TABLE I

Compounds of the formula:

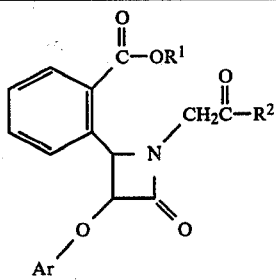

| Comp. | Ar | $R^1$ | $R^2$ | Physical State | %C Calc. | %C Fd. | %H Calc. | %H Fd. | %N Calc. | %N Fd. |
|---|---|---|---|---|---|---|---|---|---|---|
| 1 40081 | phenyl | —CH$_3$ | —OCH$_2$CH$_3$ | orange gummy solid | 65.79 | 65.25 | 5.52 | 5.59 | 3.65 | 3.47 |
| 2 40529 | 4-Cl-C$_6$H$_4$ | —CH$_3$ | —OCH$_2$CH$_3$ | dark brown gum | 57.49 | 60.17 | 4.82 | 5.45 | 3.35 | 3.32 |
| 3 40831 | 4-CH$_3$-C$_6$H$_4$ | —CH$_3$ | —OCH$_2$CH$_3$ | off-white solid, mp 102–105° C. | 66.49 | 65.75 | 5.83 | 5.75 | 3.52 | 3.32 |
| 4 40832 | 3-CH$_3$-C$_6$H$_4$ | —CH$_3$ | —OCH$_2$CH$_3$ | off-white solid, mp 74–77° C. | 66.49 | 66.84 | 5.83 | 6.29 | 3.52 | 3.17 |
| 5 40833 | 2-CH$_3$-C$_6$H$_4$ | —CH$_3$ | —OCH$_2$CH$_3$ | off-white solid, mp 96–101° C. | 66.49 | 66.43 | 5.83 | 6.35 | 3.52 | 3.20 |
| 6[a] 40899 | 2-Cl-C$_6$H$_4$ | —CH$_3$ | —OCH$_2$CH$_3$ | white solid, mp 113–116° C. | 60.36 | 60.29 | 4.82 | 4.64 | 3.35 | 3.32 |
| 7[b] 40900 | 2,4,5-trichlorophenyl | —CH$_3$ | —OCH$_2$CH$_3$ | brown gum | 51.82 | 52.35 | 3.73 | 3.69 | 2.88 | 2.58 |
| 8[a] 40901 | 3-CF$_3$-C$_6$H$_4$ | —CH$_3$ | —OCH$_2$CH$_3$ | dirt-colored solid, mp 83–85° C. | 58.54 | 57.74 | 4.47 | 4.28 | 3.10 | 3.01 |
| 9[c] 40902 | 2,4-Cl$_2$-C$_6$H$_3$ | —CH$_3$ | —OCH$_2$CH$_3$ | brown gum | 55.77 | 54.87 | 4.23 | 4.34 | 3.10 | 3.05 |
| 10[c] 41153 | 2,3,5-trichlorophenyl | —CH$_3$ | —OCH$_2$CH$_3$ | brown gum | 51.82 | 49.50 | 3.73 | 3.55 | 2.88 | 2.34 |
| 11 41154 | 4-Br-C$_6$H$_4$ | —CH$_3$ | —OCH$_2$CH$_3$ | white solid, mp 113–115° C. | 54.56 | 54.34 | 4.36 | 4.65 | 3.03 | 3.17 |
| 12 41155 | 4-Cl-2-CH$_3$-C$_6$H$_3$ | —CH$_3$ | —OCH$_2$CH$_3$ | brown gum | 61.12 | 61.31 | 5.13 | 5.32 | 3.24 | 3.28 |

TABLE I-continued

Compounds of the formula: 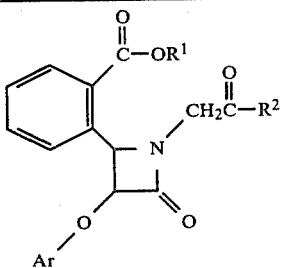

| Comp. | Ar | R¹ | R² | Physical State | %C Calc. | %C Fd. | %H Calc. | %H Fd. | %N Calc. | %N Fd. |
|---|---|---|---|---|---|---|---|---|---|---|
| 13 41297 | NO₂—⟨⟩— | —CH₃ | —OCH₂CH₃ | amber gum | 58.88 | 55.68 | 4.71 | 4.78 | 6.54 | 6.47 |
| 14 41580 | 3-NO₂-C₆H₄— | —CH₃ | —OCH₂CH₃ | orange/yellow sticky solid | 58.88 | 58.01 | 4.70 | 4.84 | 6.54 | 6.54 |
| 15 41735 | 2-F-C₆H₄— | —CH₃ | —OCH₂CH₃ | tan solid, mp 102–104° C. | 62.84 | 62.23 | 5.02 | 5.40 | 3.49 | 3.44 |
| 16 41736 | F—⟨⟩— | —CH₃ | —OCH₂CH₃ | amber gum | 62.84 | 60.09 | 5.02 | 5.32 | 3.49 | 3.20 |
| 17 41737 | 3-F-C₆H₄— | —CH₃ | —OCH₂CH₃ | amber gum | 62.8 | 61.40 | 4.99 | 5.29 | 3.5 | 3.74 |
| 18 41738 | 2-CF₃-C₆H₄— | —CH₃ | —OCH₂CH₃ | brown gum | 58.5 | 56.43 | 4.43 | 4.63 | 3.1 | 3.26 |
| 19 41969 | Cl—⟨⟩— | —CH₂CH₃ | —OCH₂CH₃ | off-white solid, mp 64–67° C. | 61.18 | 61.09 | 5.13 | 5.47 | 3.24 | 3.2 |
| 20 41970 | C₆H₅— | —CH₂CH₃ | —OCH₂CH₃ | yellow solid, mp 65–70° C. | 66.49 | 65.77 | 5.83 | 6.09 | 3.52 | 3.46 |
| 21 42111 | Cl—⟨⟩— | —CH₃ | —OCH₃ | white solid, mp 88–91° C. | 59.49 | 59.39 | 4.49 | 4.63 | 3.47 | 3.58 |
| 22 42112 | Cl—⟨⟩— | —CH₃ | —NHCH₂COCH₂CH₃ (O) | white solid, mp 135–140° C. | 58.18 | 56.88 | 4.86 | 4.6 | 5.90 | 5.44 |
| 23 42113 | C₆H₅— | —CH₃ | —NHCH₂COCH₂CH₃ (O) | brown gum | 62.72 | 64.34 | 5.49 | 5.55 | 6.36 | 6.07 |
| 24 42276 | Cl—⟨⟩— | —CH₃ | —OCH₂—C₆H₅ | white solid, mp 122–126° C. | 65.07 | 66.42 | 4.62 | 4.83 | 2.92 | 3.13 |
| 25 42277 | C₆H₅— | —CH₃ | —OCH₂—C₆H₅ | white solid, mp 99–102° C. | 70.11 | 71.04 | 5.20 | 5.35 | 3.14 | 3.18 |
| 26 42278 | 3-F-C₆H₄— | —CH₃ | —OCH₃ | off-white solid, mp 76–77° C. | 62.01 | 62.5 | 4.68 | 4.77 | 3.62 | 3.63 |

TABLE I-continued

Compounds of the formula:

[Structure: benzene ring with C(=O)-OR¹ group and attached to N-containing 4-membered ring (β-lactam) with CH₂C(=O)-R² on N, and O-Ar substituent]

| Comp. | Ar | R¹ | R² | Physical State | %C Calc. | %C Fd. | %H Calc. | %H Fd. | %N Calc. | %N Fd. |
|---|---|---|---|---|---|---|---|---|---|---|
| 27 42279 | F—⌬— | —CH₃ | —OCH₃ | white solid, mp 70–74° C. | 62.01 | 62.82 | 4.68 | 4.94 | 3.62 | 3.73 |
| 28 42736 | Cl—⌬— | —CH₂—⌬ | —OCH₂CH₃ | off-white solid, mp 91–94° C. | 65.65 | 65.99 | 4.90 | 5.1 | 2.85 | 2.95 |
| 29 42737 | ⌬— | —CH₂—⌬ | —OCH₂CH₃ | tan solid, mp 73–77° C. | 70.42 | 70.47 | 5.47 | 5.73 | 3.04 | 3.15 |

Note:
Unless noted otherwise, compounds are believed to be essentially pure trans isomer, as determined by NMR.
[a]about 95% trans by NMR
[b]about 85% trans by NMR
[c]about 80% trans by NMR

TABLE II

| Compound | ABI | GSD-MB | GSD-BG | EE | C DEF. | C DES. | CRInh. |
|---|---|---|---|---|---|---|---|
| 1 40081 | 96[a] | 0[b] | 65[b] | 0[c] | 50 | 0 | 90 |
| 2 40529 | 90[a] | 86[b] | 55[b] | 25[c] | 0 | 0 | 45 |
| 3 40831 | 0[a] | 0[b] | 0[b] | 55[d] | 0 | 0 | 0 |
| 4 40832 | 45[a] | 46[b] | 23[b] | 46[d] | 0 | 0 | 40 |
| 5 40833 | 65[a] | 21[b] | 23[b] | 123[d] | 0 | 0 | 0 |
| 6 40899 | 85[a] | 0[b] | 0[b] | 0[d] | 0 | 0 | 60 |
| 7 40900 | 72[a] | 0[b] | 0[b] | 0[d] | 0 | 0 | 83 |
| 8 40901 | 70[a] | 52[b] | 28[b] | 74[d] | 0 | 25 | 70 |
| 9 40902 | 90[a] | 85[b] | 61[b] | 132[d] | 0 | 50 | 100 |
| 10 41153 | 0 | 0 | 0 | 114 | 0 | 0 | 0 |
| 11 41154 | 80 | 0 | 0 | 29 | 0 | 0 | 0 |
| 12 41155 | 0 | 77 | 63 | 339 | 0 | 0 | 80 |
| 13 41297 | 0 | 0 | 0 | 27 | 0 | 0 | 0 |
| 14 41580 | 0 | 0 | 0 | 135 | 50 | 0 | 35 |
| 15 41735 | 95 | 0 | 0 | 11 | 0 | 0 | 60 |
| 16 41736 | 95 | 71 | 36 | 36 | 0 | 0 | 80 |
| 17 41737 | 95 | 43 | 23 | 33 | 0 | 0 | 80 |
| 18 41738 | 0 | 0 | 0 | 44 | 0 | 0 | 40 |
| 19 41969 | 85 | 0 | 0 | 11 | 0 | 0 | 0 |
| 20 41970 | 98 | 0 | 0 | 11 | 0 | 0 | 0 |
| 21 42111 | 100 | 29 | 0 | 19 | 0 | 0 | 80 |
| 22 42112 | 60 | 93 | 80 | 63 | 0 | 0 | 95 |
| 23 42113 | 0 | 57 | 30 | 21 | 0 | 0 | 0 |
| 24 42276 | 80 | 82 | 71 | 88 | 0 | 0 | 85 |
| 25 42277 | 85 | 0 | 0 | 46 | 0 | 0 | 85 |
| 26 42278 | 85 | 27 | 50 | 15 | 0 | 40 | 85 |
| 27 42279 | 85 | — | 57 | 26 | — | — | 90 |
| 28 42736 | NT | NT | NT | NT | NT | NT | NT |
| 29 42737 | NT | NT | NT | NT | NT | NT | NT |

[a]at 625 ppm
[b]at 40 ppm
[c]at 250 ppm
[d]at 100 ppm
ABI = Axillary Bud Growth Inhibition
GSD-MB = Germination & Seed Development - Mung Bean
GSD-BG = Germination & Seed Development Barnyard grass
EE = Ethylene Evolution
C DEF = Cotton Defoliation
C DES = Cotton Desiccation
CRInh = Cotton Regrowth Inhibition
NT = Not Tested

What is claimed is:

1. A compound of the formula:

[Structure: benzene with CO₂R¹ group attached to β-lactam ring bearing CH₂C(=O)-R² on N and O-Ar substituent]

wherein R¹ is lower alkyl or benzyl; R² is lower alkoxy, benzyloxy or the group $$-NHCH_2\overset{O}{\underset{\|}{C}}R^3$$

where R³ is lower alkoxy; and Ar is phenyl optionally substituted with 1 to 3 substituents independently selected from halogen, trihalomethyl, nitro and lower alkyl.

2. A compound according to claim 1 wherein the compound is the trans isomer.

3. A compound according to claim 1 wherein Ar is phenyl optionally substituted with up to two halogen atoms.

4. A compound according to claim 3 wherein Ar is phenyl substituted with one halogen atom.

5. A compound according to claim 4 wherein Ar is the group

X—⌬— wherein X is halogen.

6. A compound according to claim 5 wherein $R^2$ is lower alkoxy.

7. A compound according to claim 6 wherein X is fluoro.

8. A compound according to claim 7 wherein $R^1$ is methyl or ethyl and $R^2$ is methoxy or ethoxy.

9. A compound according to claim 8 wherein $R^1$ is methyl and $R^2$ is ethoxy.

10. A compound according to claim 9 wherein the compound is the trans isomer.

11. A compound according to claim 8 wherein $R^1$ is methyl and $R^2$ is methoxy.

12. A compound according to claim 1 wherein $R^2$ is lower alkoxy or benzyloxy.

13. A compound according to claim 12 wherein Ar is phenyl optionally substituted with up to two halogen atoms.

14. A compound according to claim 13 wherein $R^2$ is benzyloxy.

* * * * *